United States Patent [19]

Fawzi et al.

[11] Patent Number: 4,621,075

[45] Date of Patent: Nov. 4, 1986

[54] GEL-FORM TOPICAL ANTIBIOTIC COMPOSITIONS

[75] Inventors: Mahdi B. Fawzi, Flander, N.J.; Gary L. Manring, Oxford, Ohio

[73] Assignee: The Procter & Gamble Company, Cincinnati, Ohio

[21] Appl. No.: 676,027

[22] Filed: Nov. 28, 1984

[51] Int. Cl.4 ............................................. A61K 31/70
[52] U.S. Cl. ................................................ 514/32
[58] Field of Search ................................. 514/32, 24

[56] References Cited

U.S. PATENT DOCUMENTS

| | | | |
|---|---|---|---|
| 3,435,025 | 3/1969 | Birkenmeyer | 260/210 |
| 3,475,407 | 10/1969 | Birkenmeyer | 260/210 |
| 3,487,068 | 12/1969 | Morozowich et al. | 260/210 |
| 3,574,830 | 4/1974 | Roser | 514/24 |
| 3,856,943 | 12/1974 | Birkenmeyer | 260/210 |
| 3,969,516 | 7/1976 | Stoughton | 514/24 |
| 4,214,000 | 7/1980 | Papa | 514/495 |
| 4,261,982 | 4/1981 | Leudders et al. | 514/495 |

FOREIGN PATENT DOCUMENTS 1369622  10/1974  United Kingdom .

Primary Examiner—Stanley J. Friedman
Attorney, Agent, or Firm—Steven J. Goldstein; Jack D. Schaeffer; Richard C. Witte

[57] ABSTRACT

Topical pharmaceutical compositions, containing clindamycin phosphate, a zinc fatty acid salt, such as zinc acetate, and a non-aqueous vehicle, are disclosed. The compositions provide antibiotic performance and are present as physically stable, aesthetically-pleasing, clear, ringing gels, without requiring the use of conventional gelling agents. The method of topically treating clindamycin responsive dermatoses, such as acne, using these compositions is also disclosed.

6 Claims, No Drawings

GEL-FORM TOPICAL ANTIBIOTIC COMPOSITIONS

TECHNICAL FIELD

The present invention relates to pharmaceutical antibiotic compositions for topical administration, in the form of physically stable gels, which contain clindamycin phosphate.

BACKGROUND OF THE INVENTION

Antimicrobial and antibiotic agents play an important role in current medical therapy regimens. This is particularly true in dermatology where the most effective course of treatment for skin, mucous membrane or hair lesions or infections frequently includes the use of topical antibiotic agents. For example, tetracycline or clindamycin compositions, applied topically, are frequently used in the treatment of acne. The present invention encompasses topical clindamycin phosphate-containing compositions which provide effective antimicrobial performance. These compositions exist in the form of physically stable, aesthetically-pleasing, clear, ringing gels, the formation of which does not require the use of gelling agents which are generally required to form pharmaceutical gels.

Clindamycin derivatives have been disclosed for use in the topical treatment of skin disorders, such as acne. U.S. Pat. No. 3,969,516, Stoughton, issued July 13, 1976, describes a method for treating acne by topically applying antibiotics of the lincomycin family, such as clindamycin phosphate. This patent does not deal with the formulation of clindamycin gels. U.S. Pat. No. 3,487,068 describes the use of clindamycin gels using conventional gelling agents. U.S. Pat. No. 3,856,943, Birkenmeyer, issued Dec. 24, 1974, describes 1'-(beta-hydroxyethyl)-1'-demethylclindamycin compositions which are particularly effective in the treatment of urinary tract infections. These clindamycin analogs can be present as phosphoric acid salts and may be used together with antifungal agents, such as undecylenic acid and sodium caprylate.

Zinc salts of various pharmaceutical actives have also been taught to be effective in the topical treatment of acne. U.S. Pat. No. 4,261,982, Luedders and Willins, issued April 14, 1981, relates to zinc erythromycin compositions which may be administered topically for the treatment of acne. These zinc erythromycin compositions can be formed by combining an erythromycin compound with a zinc salt, such as zinc acetate, zinc propionate, or zinc valerate. There is no disclosure in this patent of gel formulations or of clindamycin-containing compositions. U.S. Pat. No. 4,214,000, Papa, issued July 22, 1980, describes the zinc salt of all-trans-retinoic acid; this compound is taught to exhibit anti-acne efficacy with reduced skin flaking and irritation when compared to conventional retinoic acid therapy. The preferred formulation taught is an alcohol-based gel; all gel formulations described require the presence of conventional gelling agents in order to achieve the desired gel properties. British Patent Specification No. 1,369,622, Shionogi & Co., Ltd., published Oct. 9, 1974, describes pharmaceutical compositions, in the form of stabilized aqueous suspensions of complex gels, which provide protracted corticotropic activity. These compositions comprise a corticotropinactive polypeptide combined with heavy metal compounds (for example, zinc acetate, zinc chloride or zinc hydroxide) and certain nitrogen-containing compounds (such as ethylene diamine). This reference does not describe clindamycin-containing compositions in any form.

However, none of this art suggests that the critical selection and combination of clindamycin phosphate with specific zinc carboxylates in non-aqueous vehicles provide a unique gel-form topical antibiotic composition. In fact, while gels are widely recognized to be a desirable form for a topical composition, most of the gels described in the art require the presence of conventional gelling agents, such as acidic carboxy polymers, to obtain the desired gel properties.

It is, therefore, an object of the present invention to provide effective topical antibiotic compositions containing clindamycin phosphate which are in the form of physically stable, aesthetically-pleasing gels.

It is a further object of the present invention to permit the formulation of clindamycin-containing topical pharmaceutical gel compositions without requiring the use of conventional gelling agents.

It is a still further object of the present invention to provide a method for the effective topical treatment of acne, as well as other clindamycin responsive dermatoses.

SUMMARY OF THE INVENTION

The present invention provides gel-form pharmaceutical antibiotic compositions for topical application comprising a safe and effective amount of clindamycin phosphate, a zinc salt of a $C_1$-$C_{20}$ fatty acid (such as zinc acetate), wherein the molar ratio of clindamycin phosphate to zinc carboxylate is from about 1:1.2 to about 1:2, and from about 85% to about 99.5% of a non-aqueous pharmaceutically-acceptable vehicle (such as ethanol, or mixtures of ethanol with diisopropyl sebacate).

In another aspect, the present invention provides a method for treating acne, as well as other clindamycin responsive dermatoses, wherein a safe and effective amount of the composition described above is topically applied to the afflicted situs.

DETAILED DESCRIPTION OF THE INVENTION

The phrase "safe and effective amount", as used herein, means sufficient clindamycin phosphate component or topical antibiotic composition to provide a desirable antibiotic effect, at a reasonable benefit/risk ratio attendant with any medical treatment. Within the scope of sound medical judgment, the required dosage of clindamycin phosphate or antibiotic composition will vary with the nature and severity of the condition being treated, the duration of the treatment, the nature of adjunct treatment, the age and physical condition of the patient, the nature of the vehicle utilized in the composition, and like considerations more fully discussed hereinafter.

"Pharmaceutically-acceptable", as used herein, means that the zinc carboxylate and vehicle components, as well as other ingredients included in the compositions, are suitable for use in contact with the tissues of humans and lower animals without undue toxicity, irritation, allergic response, and the like, commensurate with a reasonable benefit/risk ratio.

The term "comprising", as used herein, means that various other compatible drugs and medicaments, as well as inert ingredients, can be conjointly employed in the compositions and methods of this invention, as long as the critical clindamycin phosphate, zinc carboxylate and non-aqueous vehicle components are used in the manner disclosed. The term "comprising" thus includes the more restrictive terms "consisting of" and "consisting essentially of".

By "compatible" is meant that the components of the present invention are capable of being commingled without interacting in a manner which would substantially decrease the availability and/or efficacy of the clindamycin phosphate under ordinary use conditions.

All percentages and ratios used herein are by weight, unless otherwise specified.

Compositions of the present invention contain a safe and effective amount of clindamycin phosphate as the antibacterial component. Under most conditions, this will translate into compositions which contain from about 0.25% to about 5% of the clindamycin phosphate component. Preferred compositions contain from about 0.5% to about 2%, most preferably from about 1%, of clindamycin phosphate. It is also preferred that the total concentration of the mixture of clindamycin phosphate together with zinc salt not exceed about 3% of the composition in order to assure solubility in the vehicle.

Clindamycin phosphate, the phosphate derivative of clindamycin, is well-known in the pharmaceutical arts. It is clindamycin 2-(dihydrogen phosphate) and has the formula $C_{18}H_{34}ClN_2O_8PS$. Clindamycin phosphate is described in Martindale, *The Extra Pharmacopoeia*, 28th edition (1982), The Pharmaceutical Press, pages 1147–1148, incorporated herein by reference. It is a white to off-white, essentially odorless, hygroscopic crystalline powder with a bitter taste. Clindamycin phosphate is soluble in water, slightly soluble in dehydrated alcohol, very slightly soluble in acetone, and practically insoluble in chloroform and ether.

The uses, properties and methods of synthesis, of clindamycin and its various derivatives are set forth in U.S. Pat. No. 3,969,516, Stoughton, issued July 13, 1976; Magerlein, et al, *Antimicro. Ag. Chemother.* (1966) 727; U.S. Pat. No. 3,475,407, Birkenmeyer, issued in 1969; U.S. Pat. Nos. 3,509,127 and 3,544,551, Kagan and Magerlein, issued in 1970; U.S. Pat. No. 3,513,155, Birkenmeyer and Kagan, issued in 1970; Birkenmeyer and Kagan, *J. Med. Chem.* 13, 616(1970); Oesterling, *J. Pharm. Sci.* 59, 63(1970); McGehee, et al, *Am. J. Med. Sci.* 256, 279 (1968); D. A. Leigh, *J. Antimicrob. Chemother.* 7 (*Supplement A*), 3(1981); J. E. Gray, et al, *Toxicol. Appl. Pharmacol.* 21, 516(1972); and L. W. Brown and W. F. Beyer in *Analytical Profiles of Drug Substances*, Vol. 10, K. Florey, editor (Academic Press, New York, 1981) pages 75–91, (all of the foregoing references being incorporated herein by reference).

The critical selection of zinc carboxylates, component ratios and non-aqueous vehicles, when combined with clindamycin phosphate, provides effective antibiotic compositions which exist in the form of physically stable gels, without requiring the use of conventional gelling agents. To form these gels of the present invention, the clindamycin phosphate must be combined with a zinc carboxylate selected from zinc salts of $C_1$–$C_{20}$ fatty acids. These acids are well-known in the art. They may be branched or straight chain, mono- or polycarboxylic, saturated or unsaturated, or cyclic (e.g., benzoic acid) or open chain. The zinc salts of cis and trans retinoic acid (3,7-dimethyl-9-(2,6,6-trimethyl-1-cyclohexen-1-yl)-2,4,6,8-nonatetraenoic acid; Vitamin A acid) may be used as the zinc carboxylate herein.

Preferred zinc salts are formed from $C_1$–$C_{20}$ straight chain mono-carboxylic acids, such as zinc formate, zinc acetate, zinc propionate, zinc valerate, zinc octoate, zinc oleate, zinc undecylenate, or mixtures thereof. Particularly preferred zinc salts include zinc formate, zinc acetate, zinc propionate, zinc valerate, zinc octoate or mixtures thereof, especially zinc acetate.

The clindamycin phosphate and zinc carboxylate components are combined in molar ratios of clindamycin phosphate:zinc carboxylate of from about 1:1.2 to about 1:2, most preferably about 1:1.5. Formulations having ratios below about 1:1.2 result in poor or no gel formation. In such compositions, the clindamycin phosphate and zinc salt are generally soluble, but the mixture remains a liquid. Formulations having ratios above about 1:2 will result in poor solubility of the zinc salt in the gels (i.e., cloudy, non-homogeneous gels).

The compositions of the present invention also contain from about 85% to about 99.5%, preferably from about 95% to about 98.5% of a compatible non-aqueous pharmaceutically-acceptable topical vehicle. Although it is preferred that these vehicles be free of water, the compositions of the present invention may contain up to about 5% water without significant adverse effects on the formation of the desired gels. These non-aqueous vehicle components are also well-known in the pharmaceutical arts, and they include (but are not limited to) short chain alcohols and ketones and emollients, such as hydrocarbon oils and waxes, lanolin and lanolin derivatives, silicone oils, monoglyceride, diglyceride, and triglyceride esters, fatty alcohols, alkyl and alkenyl esters of fatty acids, alkyl and alkenyl diesters of dicarboxylic acids, polyhydric alcohols and their ether and ester derivatives; wax esters and beeswax derivatives. Preferred vehicles incorporate methanol, ethanol, n-propanol, isopropanol, butanol, polypropylene glycol, polyethylene glycol and mixtures of these components. Particularly preferred vehicles include ethanol, n-propanol and butanol, especially ethanol. These preferred solvents may also be combined with other components, such as diisopropyl sebacate, isopropyl myristate, methyl laurate, silicone, glycerine and mixtures of these components, to provide non-aqueous vehicles which are also useful in the present invention. Of these additional components, diisopropyl sebacate is especially useful. In fact, preferred vehicles include mixtures of ethanol and diisopropyl sebacate in ratios, by weight, of from about 4:1 to about 1:4. Preferred vehicles contain from about 15% to about 35% diisopropyl sebacate and from about 65% to about 85% ethanol.

Compositions of the present invention may additionally contain, at their art-established usage levels, compatible adjunct components conventionally used in the formulation of topical pharmaceutical compositions. These adjunct components may include, but are not limited to, pharmaceutically-active materials (such as supplementary antimicrobial or anti-inflammatory ingredients, e.g., steroids) or ingredients used to enhance the formulation itself (such as excipients, dyes, perfumes, skin penetration enhancers, stabilizers, preservatives, and antioxidants). Since the compositions of the present invention permit the formation of gels without requiring the presence of conventional gelling agents, such agents are preferably not included. Examples of such agents include the pharmaceutically-acceptable acidic carboxy polymers, such as the Carbopol compounds commercially available from B. F. Goodrich Chemicals, Cleveland, Ohio.

The gel-form compositions of the present invention may be formulted by the conventional mixing of the components described above. However, it is preferred that the clindamycin phosphate be added to the vehicle and stirred for several minutes prior the addition of the zinc carboxylate component. which is subsequently added and completely mixed into the composition. The zinc carboxylate component may be added as a solid (e.g., zinc acetate) or a liquid (e.g., zinc octanoate or zinc oleate). Gel formation takes place within from about 2 minutes to about 16 hours after mixing, depending upon the components utilized. Higher temperatures, the use of high shear mixing, the presence of water in the system, and small zinc carboxylate particle size may adversely affect the formation of the desired gels. Although not intending to be bound by theory, it is believed that the combination of clindamycin phosphate and the defined zinc carboxylates within the required ratios forms zinc coordination polymers of the clindamycin, having the desired gel properties.

In formulating stable and effective topical compositions containing clindamycin phosphate, several additional techniques may also be useful. The solubility of mixtures of clindamycin phosphate (as well as other water-soluble pharmaceutical actives) with zinc salts in non-aqueous vehicles may be improved by the addition of low levels of amines, such as monoethanolamine or diisopropylamine. In addition, the solubility of mixtures of zinc salts with clindamycin phosphate or clindamycin hydrochloride may be enhanced in hydroalcoholic vehicles by the addition of small amounts of water-soluble alpha-hydroxy or polycarboxylic acids, such as citric acid, lactic acid, malonic acid, maleic acid, and gentisic acid.

Topical treatment regimens according to the practice of this invention comprise applying the compositions herein directly to the skin at the situs of the dermatosis. The dermatoses which may be treated using the present invention include acne and acneiform skin diseases, as well as other skin disorders of bacterial origin (i.e., clindamycin responsive dermatoses). The topical treatment regimen encompassed herein includes both human and veterinary uses. In addition to acne, skin conditions which may be usefully treated using the method of the present invention include, but are not limited to, impetigo (impetigo contagiosa) or ecthyma; bullous impetigo; scalded skin syndrome (dermatitis exfoliative); erysipelas; folliculitis (including furuncles/carbuncles); hidradentitis suppurativa; paronychial infections; erythrasma; and the like.

The rate of application and duration of treatment will depend upon the severity and nature of the condition, the response of the particular patient, and related factors within the sound medical judgment of an attending physician or the patient. In general, for the compositions within the compositional ranges noted above, application rates of from about 0.01 milligrams/centimeter$^2$ to about 25 milligrams/centimeter$^2$ per day are used. Application can be made once, or preferably several times, daily for periods of a week or more, to relieve the condition being treated.

The following non-limiting examples illustrate the pharmaceutical compositions and methods of treatment of the present invention.

EXAMPLE I

A 100 gram batch of a gel of the present invention, having the following composition, is prepared as described.

| Component | % (by weight) |
| --- | --- |
| Clindamycin phosphate | 1.0 |
| Zinc acetate (anhydrous) | 0.5 |
| Diisopropyl sebacate | 28.0 |
| Ethanol (anhydrous) | 70.5 |

Clindamycin Phosphate:Zinc Acetate = 1:1.38 molar 28.0 g diisopropyl sebacate is weighed into a beaker. 70.5 g ethanol is then weighed out and added to the beaker. These two components are then mixed together with moderate agitation using a magnetic stirrer. The beaker is kept covered during mixing in order to minimize ethanol evaporation. 1.0 g clindamycin phosphate is added to the beaker and stirring is continued for about two minutes. 0.5 g zinc acetate is then added and the stirring is continued until the mixture thickens. The stirring bar is removed and the mixture is set aside. After several hours, a clear gel, having antimicrobial properties, is formed. When this gel is applied topically to skin area affected with acne vulgaris, at a rate of about 10 mg/cm$^2$ for three to four weeks, the acne condition is effectively treated.

Substantially similar results are obtained where the zinc acetate in the above example is replaced, in whole or in part, by zinc formate, zinc propionate, zinc valerate, zinc octoate, zinc undecylenate, zinc benzoate, or mixtures thereof. Similar results are also obtained when the ethanol in the above example is replaced, in whole or in part, by methanol, n-propanol, isopropanol, propylene glycol, polyethylene glycol, butanol, or mixtures thereof. Similar results are also obtained when the diisopropyl sebacate in the above example is replaced, in whole or in part, by isopropyl myristate, propylene glycol, polyethylene glycol, methyl laurate, silicone, glycerine, or mixtures thereof. Effective antimicrobial gels are also formed when the above formulation is adjusted such that the molar ratio of clindamycin phosphate:zinc acetate is 1:1.2; 1:1.3; 1:1.5; 1:1.7; 1:1.85 or 1:2.

EXAMPLE II

A 100 gram batch of a gel of the present invention, having the following composition, is prepared according to the procedure described in Example I (substituting zinc propionate for zinc acetate and polyethylene glycol for diisopropyl sebacate).

| Component | % (by weight) |
| --- | --- |
| Clindamycin phosphate | 1.0 |
| Zinc propionate (anhydrous) | 0.6 |
| Polyethylene glycol 400 | 25.0 |
| Ethanol (anhydrous) | 73.4 |

Clindamycin Phosphate:Zinc Propionate = 1:1.43 molar

This gel composition, when applied topically, provides effective treatment for clindamycin responsive dermatoses.

EXAMPLE III

A 100 gram batch of a gel of the present invention, having the following composition, is prepared. The procedure utilized is the same as that described in Example I except: (1) zinc acetate dihydrate is substituted for anhydrous zinc acetate; (2) propylene glycol is substituted for diisopropyl sebacate; and (3) methyl laurate is added to the mixture after ethanol and before the clindamycin phorphate and zinc acetate components.

| Component | % (by weight) |
|---|---|
| Clindamycin phosphate | 1.00 |
| Zinc acetate (dihydrate) | 0.65 |
| Methyl laurate | 5.00 |
| Propylene glycol | 25.00 |
| Ethanol (anhydrous) | 68.35 |

Clindamycin Phosphate:Zinc Acetate = 1:1.5 molar

This gel composition, when applied topically, provides effective treatment for acne vulgaris, as well as other clindamycin responsive dermatoses.

EXAMPLE IV

A 100 gram batch of a gel of the present invention, having the following composition, is prepared according to the procedure described in Example I (except that ethanol, rather than an ethanol/diisopropyl sebacate mixture, is the vehicle component in this formulation).

| Component | % (by weight) |
|---|---|
| Clindamycin phosphate | 0.50 |
| Zinc acetate (anhydrous) | 0.27 |
| Ethanol | 99.23 |

Clindamycin Phosphate:Zinc Acetate = 1:1.5 Molar

This gel composition, when applied topically, provides effective treatment for acne vulgaris, as well as other clindamycin responsive dermatoses.

EXAMPLE V

Clindamycin phosphate and zinc acetate (anhydrous) were formulated in a 28/72 (weight %) diisopropyl sebacate/ethanol vehicle at different molar ratios to determine the effect of molar ratio on gelling properties. The compositions formulated contained about 1.5% (by weight) of the clindamycin phosphate/zinc acetate mixture and about 98.5% (by weight) of the vehicle. In each instance clindamycin phosphate was added to the vehicle and stirred (as per Example I) for approximately 2-5 minutes before the zinc acetate was added, with additional mixing.

| Clindamycin Phosphate:Zinc Acetate (Molar) Ratios Tested |
|---|
| 1:0.5 |
| 1:1.0 |
| 1:1.5* |
| 1:2.0* |

*composition of the present invention

Formulations having ratios of 1:0.5 and 1:1.0 did not gel, even after 24 hours. Formulations having ratios of 1:1.5 and 1:2.0 did form gels. The formulation having a ratio of 1:1.5 began to gel in 25 minutes. Initially there were a few undissolved suspended particles observed in the gel, but these particles dissolved within a few hours forming a clear gel. The formulation having a ratio of 1:2.0 began to gel in 9 minutes; some undissolved particles were observed in it, but the gel formed was generally clear and homogeneous.

What is claimed is:

1. A gel-form pharmaceutical composition for topical application comprising:
   (a) from about 0.25% to about 5% of clindamycin phosphate;
   (b) zinc acetate, wherein the molar ratio of (a):(b) is from about 1:1.2 to about 1:2; and
   (c) from about 85% to about 99.5% of a non-aqueous pharmaceutically-acceptable topical vehicle which consists essentially of (1) a component selected from the group consisting of methanol, ethanol, n-propanol, butanol and mixtures thereof, together with (2) diisopropyl sebacate.

2. A composition according to claim 1 wherein the vehicle component (1) comprises ethanol.

3. A composition according to claim 1 wherein the molar ratio of (a):(b) is about 1:1.5.

4. A composition according to claim 2 wherein the vehicle component comprises a mixture of diisopropyl sebacate and ethanol in a ratio by weight of from about 4:1 to about 1:4.

5. A composition according to claim 4 wherein the molar ratio of (a):(b) is about 1:1.5.

6. A method for treating skin disorders of bacterial origin comprising applying topically at an afflicted situs a safe and effective amount of the composition according to claim 1.

* * * * *